(12) United States Patent
Ye

(10) Patent No.: US 11,721,476 B1
(45) Date of Patent: Aug. 8, 2023

(54) SENSOR COIL ASSEMBLY

(71) Applicant: St. Jude Medical International Holding S.à r.l., Luxembourg (LU)

(72) Inventor: Qingshan Ye, Plymouth, MN (US)

(73) Assignee: ST JUDE MEDICAL INTERNATIONAL HOLDING S.À R.L., Luxembourg (LU)

( * ) Notice: Subject to any disclaimer, the term of this patent is extended or adjusted under 35 U.S.C. 154(b) by 1,177 days.

(21) Appl. No.: 15/341,923

(22) Filed: Nov. 2, 2016

Related U.S. Application Data

(60) Provisional application No. 62/251,504, filed on Nov. 5, 2015.

(51) Int. Cl.
| | |
|---|---|
| *H01F 27/28* | (2006.01) |
| *A61B 5/06* | (2006.01) |
| *A61M 25/01* | (2006.01) |
| *H01F 27/32* | (2006.01) |
| *H01F 27/29* | (2006.01) |
| *H01F 41/06* | (2016.01) |
| *A61B 34/20* | (2016.01) |

(52) U.S. Cl.
CPC .......... *H01F 27/2823* (2013.01); *A61B 5/062* (2013.01); *A61M 25/0127* (2013.01); *H01F 27/29* (2013.01); *H01F 27/325* (2013.01); *H01F 27/2828* (2013.01); *H01F 41/06* (2013.01); *A61B 2034/2051* (2016.02)

(58) Field of Classification Search
CPC .......... H01F 27/325; H01F 27/28-2895; H01F 41/06; A61B 5/062; A61B 2034/2051; H01F 2005/025; H01F 41/09; A61B 5/06-068; A61M 25/0127; H01F 5/02; A61B 1/00158
See application file for complete search history.

(56) References Cited

U.S. PATENT DOCUMENTS

| | | | | |
|---|---|---|---|---|
| 7,028,387 | B1* | 4/2006 | Huynh et al. .......... | A61B 5/062 29/602.1 |
| 2002/0068868 | A1* | 6/2002 | Thompson et al. | A61M 25/0152 600/434 |
| 2003/0114844 | A1* | 6/2003 | Ormsby et al. .......... | H01Q 1/42 607/156 |
| 2005/0131387 | A1* | 6/2005 | Pursley ............ | A61M 25/0012 604/524 |
| 2011/0098559 | A1* | 4/2011 | Besz et al. ............... | A61B 5/06 600/424 |
| 2012/0101362 | A1* | 4/2012 | Weiss et al. ...... | A61M 25/0021 600/411 |
| 2013/0065767 | A1* | 3/2013 | Schauwecker et al. .. | H01F 6/06 505/211 |
| 2014/0312999 | A1* | 10/2014 | Oomen ................... | H01F 6/00 505/211 |
| 2014/0323852 | A1* | 10/2014 | Wald et al. ............ | A61B 5/062 600/424 |
| 2015/0377940 | A1* | 12/2015 | Wang et al. ............. | H01F 5/02 324/654 |
| 2016/0031673 | A1* | 2/2016 | Chen et al. ............... | H01F 5/02 242/118 |
| 2017/0042621 | A1 | 2/2017 | Wald et al. | |

* cited by examiner

Primary Examiner — Boniface Ngathi N
Assistant Examiner — Milton Truong
(74) *Attorney, Agent, or Firm* — Billion & Armitage

(57) ABSTRACT

A sensor coil assembly comprises a positioning sensor comprising a wound coil formed by a first conductive wire segment wound around a longitudinal axis. The first conductive wire segment can include a first coil end and a second coil end. A second conductive wire segment can extend from the first coil end of the first conductive wire segment. The second conductive wire segment can be wound around a first bobbin. A third conductive wire segment can extend from the second coil end of the first conductive wire segment. The third conductive wire segment can be wound around a second bobbin.

5 Claims, 9 Drawing Sheets

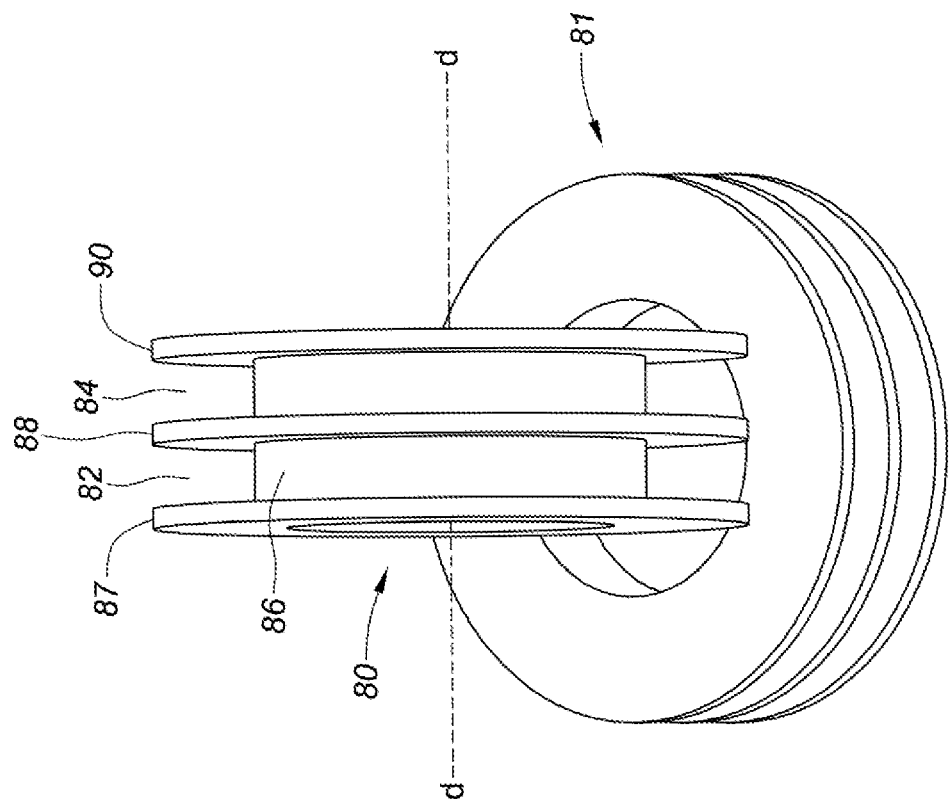
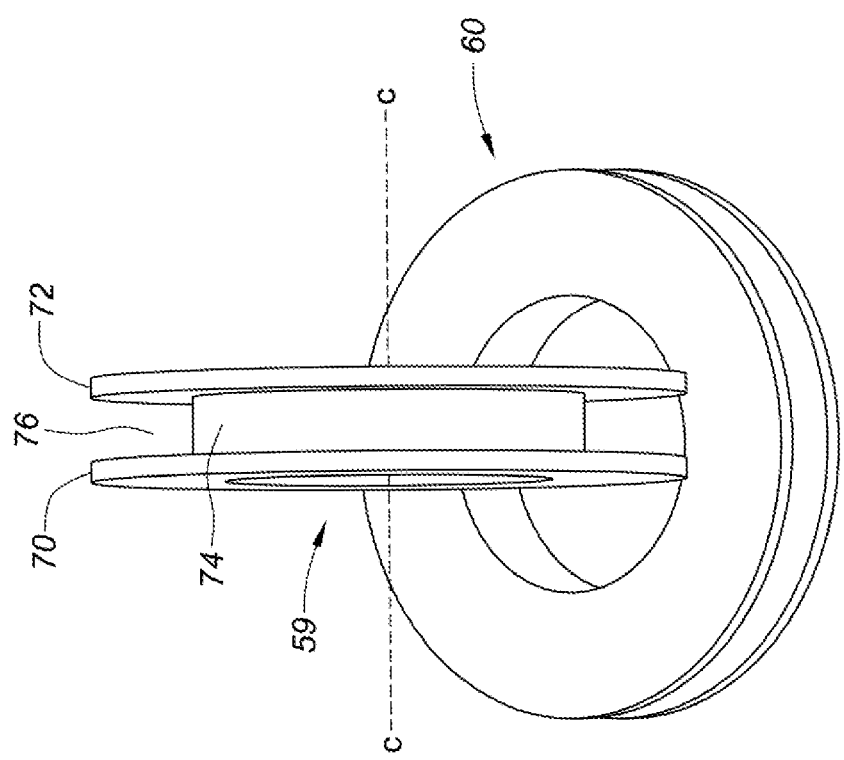
FIG. 2C
FIG. 2B

SENSOR COIL ASSEMBLY

CROSS-REFERENCE TO RELATED APPLICATIONS

This application claims the benefit of U.S. Pat. Application No. 62/251,504, filed Nov. 5, 2015, the entire contents of which is incorporated herein by reference.

BACKGROUND

A. Field

The present disclosure relates generally to a sensor coil assembly formed from a unitary piece of wire.

B. Background Art

Medical devices, catheters, and/or cardiovascular catheters, such as electrophysiology catheters can be used in a variety of diagnostic, therapeutic, mapping and/or ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart, which can lead to a variety of symptomatic and asymptomatic ailments and even death.

A medical device can be threaded through a vasculature of a patient to a site where the diagnostic, therapeutic, mapping, and/or ablative procedure to diagnose and/or correct the condition is performed. To aid in the delivery of the medical device to the site, sensors (e.g., electrodes, electromagnetic coils) can be placed on the medical device, which can receive signals that are generated proximate to the patient from a device (e.g., electromagnetic field generator). Based on the received signals, an orientation and/or position of the medical device can be computed.

BRIEF SUMMARY

Various embodiments herein provide a sensor coil assembly. In at least one embodiment, a positioning sensor can comprise a wound coil formed by a first conductive wire segment wound around a longitudinal axis. The first conductive wire segment can include a first coil end and a second coil end. A second conductive wire segment can extend from the first coil end of the first conductive wire segment. The second conductive wire segment can be wound around a first bobbin. A third conductive wire segment can extend from the second coil end of the first conductive wire segment. The third conductive wire segment can be wound around a second bobbin.

Various embodiments herein provide a catheter. In at least one embodiment, the catheter can include an elongated shaft. The elongated shaft can include a proximal portion and a distal portion. A positioning sensor comprising a wound coil can be disposed in the distal portion of the elongated shaft. The wound coil can be formed from a first conductive wire segment wound around a longitudinal axis. A second conductive wire segment can extend from a first coil end of the first wire segment and through the proximal portion. A third conductive wire segment can extend from a second coil end of the first wire segment and through the proximal portion. The first conductive wire segment, the second conductive wire segment, and the third conductive wire segment can be formed from a unitary piece of wire.

Various embodiments herein provide a distributed sensor coil assembly. In at least one embodiment, the distributed sensor coil assembly can include an origin coil formed from an origin conductive wire. A pair of origin leads can be formed from the conductive wire that extends from a proximal end of the origin coil. A terminal coil can be formed from the conductive wire and can be disposed in a spaced apart relationship with the origin coil. The terminal coil can include a pair of terminal leads that are electrically connected with the pair of origin leads via the origin coil.

Various embodiments herein provide a method for forming a sensor coil assembly from a unitary piece of wire. The method can include winding a first conductive wire segment of the unitary piece of wire around a first carrier member. The method can include winding a second conductive wire segment of the unitary piece of wire around a longitudinal axis to form a wound coil. The method can include winding a third conductive segment of the unitary piece of wire around a second carrier member.

BRIEF DESCRIPTION OF THE DRAWINGS

FIG. 2B depicts an isometric side view of the bobbins in FIG. 2A, in accordance with embodiments of the present disclosure.

FIG. 2C depicts an isometric side view of an additional embodiment of the bobbins in FIG. 2A, in accordance with embodiments of the present disclosure.

DETAILED DESCRIPTION

Figure 1:
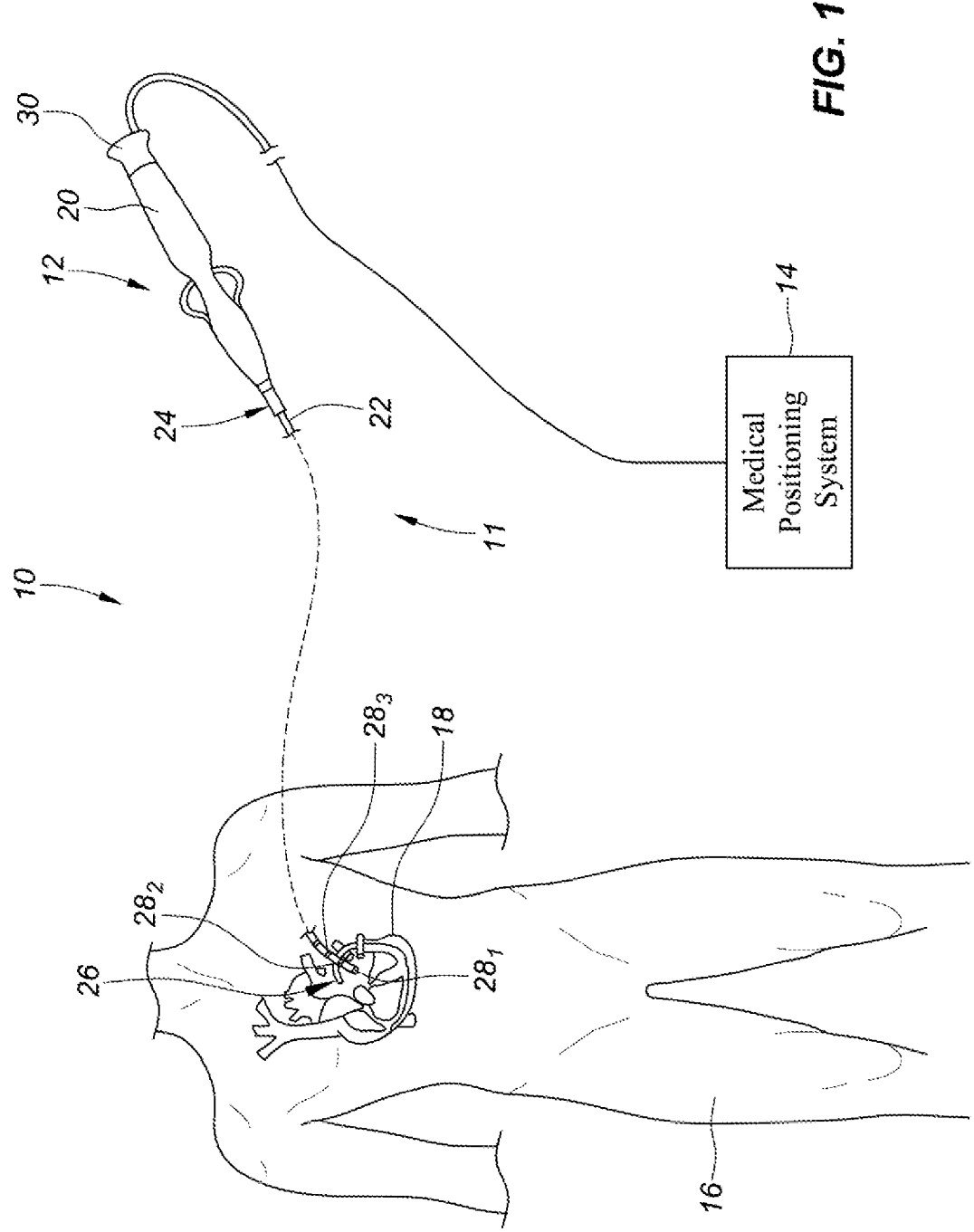
FIG. 1 depicts a diagrammatic view of an exemplary system for performing one or more diagnostic or therapeutic procedures, wherein the system comprises a magnetic field-based medical positioning system, in accordance with embodiments of the present disclosure.

In some embodiments, and with reference to FIG. 1, the system 10 can include a medical device 11 and a medical positioning system 14. The medical device 11 can include an elongate medical device such as, for example, a catheter or a sheath. For purposes of illustration and clarity, the description below will be limited to an embodiment wherein the medical device 11 comprises a catheter (e.g., catheter 12). It will be appreciated, however, that the present disclosure is not meant to be limited to such an embodiment, but rather in other exemplary embodiments, the medical device may comprise other elongate medical devices, such as, for example and without limitation, sheaths, introducers and the like. Accordingly, as used in various embodiments herein, a "catheter" includes any elongated structure that can be inserted into and/or through a body cavity, duct, and/or vessel. In at least one embodiment, a catheter may be hollow, such as an introducer or coronary catheter, and/or define a lumen therethrough for passing fluid or another medical device, such as a guidewire or another catheter, for example. However, in various embodiments, a catheter may be closed at least at its distal end, such as an electrophysiology catheter or guidewire.

With continued reference to FIG. 1, the catheter 12 can be configured to be inserted into a patient's body 16, and more particularly, into the patient's heart 18. The catheter 12 may include a handle 20 that has a proximal end 30, a shaft 22 having a proximal end portion 24 and a distal end portion 26, and one or more sensors 28 mounted in or on the shaft 22 of the catheter 12. As used herein, "sensor 28" or "sensors 28" may refer to one or more sensors $28_1$, $28_2$, ... $28_N$, as appropriate and as generally depicted. In an exemplary embodiment, the sensors 28 are disposed at the distal end portion 26 of the shaft 22. The catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

The shaft 22 can be an elongate, tubular, flexible member configured for movement within the body 16. The shaft 22 supports, for example and without limitation, sensors and/or electrodes mounted thereon, such as, for example, the sensors 28, associated conductors, and possibly additional electronics used for signal processing and conditioning. The shaft 22 may also permit transport, delivery, and/or removal of fluids (including irrigation fluids, cryogenic ablation fluids, and bodily fluids), medicines, and/or surgical tools or instruments. The shaft 22 may be made from conventional materials such as polyurethane, and define one or more lumens configured to house and/or transport electrical conductors, fluids, or surgical tools. The shaft 22 may be introduced into a blood vessel or other structure within the body 16 through a conventional introducer. The shaft 22 may then be steered or guided through the body 16 to a desired location, such as the heart 18, using means well known in the art.

The sensors 28 mounted in or on the shaft 22 of the catheter 12 may be provided for a variety of diagnostic and therapeutic purposes including, for example and without limitation, electrophysiological studies, pacing, cardiac mapping, and ablation. In an exemplary embodiment, one or more of the sensors 28 are provided to perform a location or position sensing function. More particularly, and as will be described in greater detail below, one or more of the sensors 28 are configured to be a positioning sensor that provides information relating to the location (e.g., position and orientation) of the catheter 12, and the distal end portion 26 of the shaft 22 thereof, in particular, at certain points in time. Accordingly, in such an embodiment, as the catheter 12 is moved along a surface of a structure of interest of the heart 18 and/or about the interior of the structure, the sensor(s) 28 can be used to collect location data points that correspond to the surface of, and/or other locations within, the structure of interest. These location data points can then be used for a number of purposes such as, for example and without limitation, the construction of surface models of the structure of interest.

For purposes of clarity and illustration, the description below will be with respect to an embodiment wherein a single sensor 28 of the catheter 12 comprises a positioning sensor. It will be appreciated, however, that in other exemplary embodiments, which remain within the spirit and scope of the present disclosure, the catheter 12 may comprise more than one positioning sensor as well as other sensors or electrodes configured to perform other diagnostic and/or therapeutic functions. As will be described in greater detail below, the sensor 28 can include a pair of leads extending from a sensing element thereof (e.g., a coil) that are configured to electrically couple the sensor 28 to other components of the system 10, such as, for example, the medical positioning system 14. In some embodiments, the sensing element can be an electromagnetic position sensor, such as a wound coil, which can sense a magnetic field that is generated in proximity to the patient. Depending on a position and orientation (P&O) of the electromagnetic position sensor, different electrical signals can be generated by the coil and transferred to the medical positioning system, for a determination of a location reading that can be indicative of the P&O of the electromagnetic position sensor.

The location readings may each include at least one or both of a position and an orientation (P&O) relative to a reference coordinate system, which may be the coordinate system of medical positioning system 14. For some types of sensors, the P&O may be expressed with five degrees-of-freedom (five DOF) as a three-dimensional (3D) position (i.e., a coordinate in three axes X, Y and Z) and two-dimensional (2D) orientation (e.g., an azimuth and elevation) of sensor 28 in a magnetic field relative to a magnetic field generator(s) or transmitter(s) and/or a plurality of electrodes in an applied electrical field relative to an electrical field generator (e.g., a set of electrode patches). For other sensor types, the P&O may be expressed with six degrees-of-freedom (six DOF) as a 3D position (i.e., X, Y, Z coordinates) and 3D orientation (i.e., roll, pitch, and yaw).

Figure 2A:
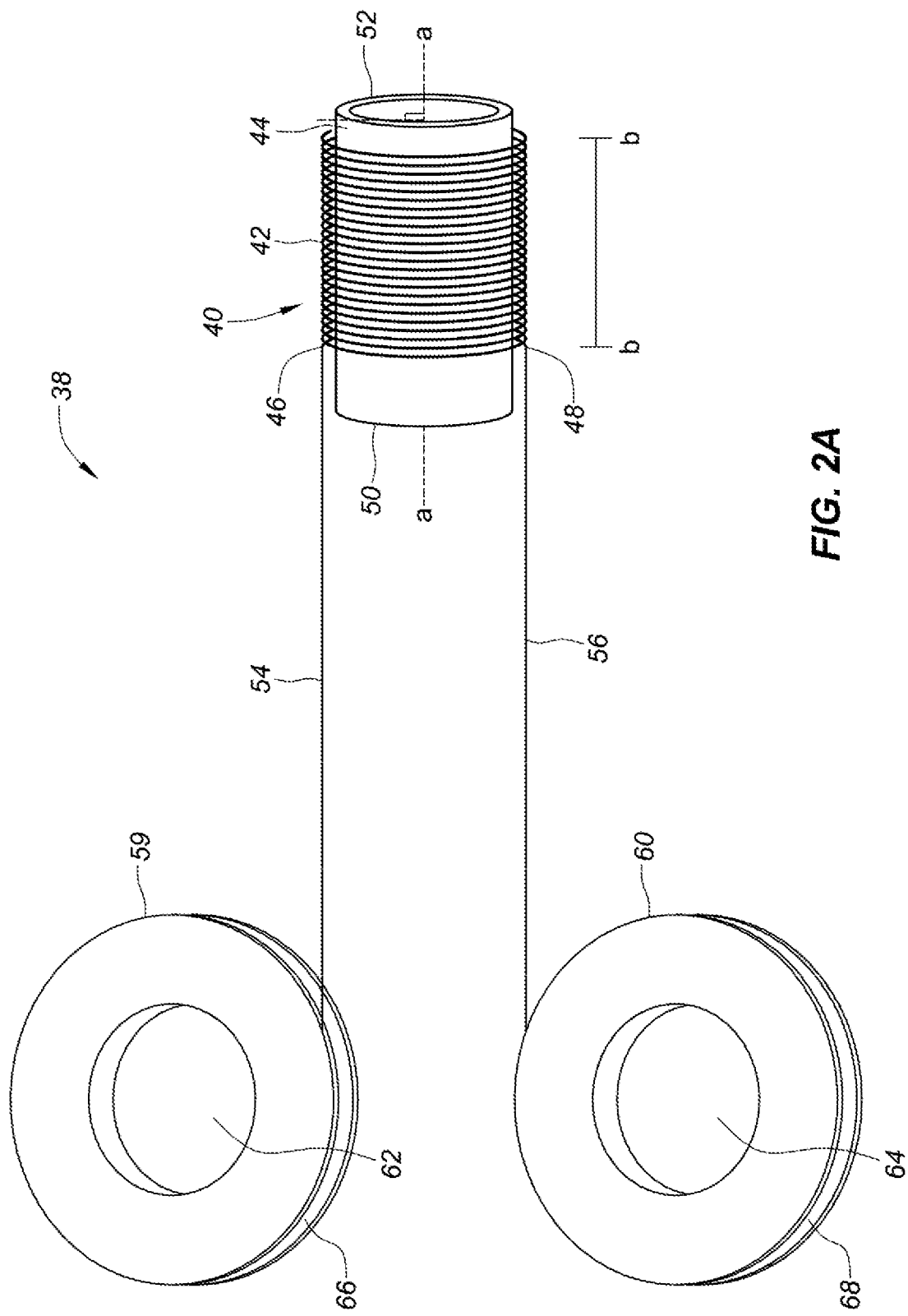
FIG. 2A depicts an isometric side and top view of a sensor coil assembly that includes a wound coil and bobbins, in accordance with embodiments of the present disclosure.

FIG. 2A is an isometric side and top view of a sensor coil assembly that includes a wound coil and bobbins, in accordance with embodiments of the present disclosure. In some embodiments, the sensor coil assembly 38 can include a wound coil 40 formed by a first conductive wire segment 42. In some embodiments, the first conductive wire segment 42 can be wound around a sensor core 44. In some embodiments, the sensor core 44 can be formed of a semi-rigid material and can be a hollow cylinder that has a longitudinal axis defined by line a-a in FIG. 2A. The first conductive wire segment 42 may be wound around an outer surface of a sensor core 44, with the windings extending along the longitudinal axis of the sensor core defined by line a-a and over a length b-b, and with the windings being coaxial with the sensor core 44. Alternatively, in some embodiments, the first conductive wire segment 42 can be wound around a longitudinal axis of the sensor coil assembly 38, but may not be wound around a sensor core 44. For example, in such an embodiment, the first conductive wire segment 42 can be wound around a winding core to form wound coil 40, and the winding core can then be removed from the wound coil 40. In some embodiments, the wound coil 40 can have a zero degree winding angle and/or a winding angle that is greater than zero degrees.

In some embodiments, the first conductive wire segment 42 can include a first coil end 46 and a second coil end 48. The first conductive wire segment 42 can be wound from a proximal end 50 of the sensor core 44 to a distal end 52 of the sensor core, in some embodiments. In some embodiments, the first conductive wire segment 42 can be wound in one or more passes between the proximal end 50 and the distal end 52 to form one or more layers of windings of the first conductive wire segment 42. In an example, the first conductive wire segment 42 can be wound from the proximal end 50 to the distal end 52 and wound back to the proximal end 50, such that ends of the first coil end 46 and the second coil end 48 are both located on the proximal end 50 of the sensor core 44. Thus, two passes would be made between the proximal end 50 and the distal end 52, forming two layers of windings.

In some embodiments, the first conductive wire segment 42 can be wound from the proximal end 50 to the distal end 52, such that the first coil end 46 is located at the proximal end 50 and the second coil end 48 is located at the distal end 52 of the sensor core. The wound coil 40 can include a plurality of layers of windings formed with the first conductive wire segment 42. In some embodiments, the wound coil 40 can include from one to eight passes to form from 1 to eight layers of wire. As such, the wound coil 40 can include from one to eight layers of wire. However, more than eight layers of wire can be used to form the wound coil 40, in some embodiments.

As discussed, the first coil end 46 and the second coil end 48 can both be located on the proximal end 50 of the sensor core 44. Alternatively, the first coil end 46 can be located on the proximal end 50 and the second coil end 48 can be located on the distal end of the sensor core 44. In some embodiments, a second conductive wire segment 54 can extend from the first coil end 46 of the first conductive wire segment 42. In addition, a third conductive wire segment 56 can extend from the second coil end 48 of the first conductive wire segment 42. In some embodiments, when the second coil end 48 is located at the distal end of the sensor, the third conductive wire segment 56 can extend from a distal end of the wound coil 40, specifically, from the second coil end 48. As shown, the first coil end 46 and the second coil end 48 extend from a proximal end of the wound coil 40.

In some embodiments, the first conductive wire segment 42, the second conductive wire segment 54, and the third conductive wire segment 56 can be formed from a unitary piece of wire. For example, the first conductive wire segment 42, the second conductive wire segment 54, and the third conductive wire segment 56 can be formed from a single piece of wire. The unitary piece of wire can include a first end and a second end. For example, the second conductive wire segment 54 can have a first end and the third conductive wire segment 56 can have a second end. In some embodiments, the unitary piece of wire can include no connections between the first end of the unitary piece of wire and the second end of the unitary piece of wire. In some embodiments, the unitary piece of wire can have a wire gauge of approximately 58 AWG. However, the wire can be of a smaller or larger wire gauge.

In some embodiments, the sensor coil assembly 38 can be included in a catheter, as further discussed herein. For example, the wound coil 40 and/or the sensor core 44 can be included in a distal portion of a catheter shaft 22. In some embodiments, the second conductive wire segment 54 and the third conductive wire segment 56 can extend through a proximal portion of the catheter shaft 22.

In prior approaches that include a wound coil in a catheter shaft, two short leads can extend from the wound coil, which can then be connected to two longer leads that extend through a proximal portion of the catheter shaft. For example, each of the two longer leads can be soldered to a respective one of the two short leads. In some cases, each of the two longer leads can be directly connected to a respective one of the two short leads. Alternatively, some approaches have used a small printed circuit board that includes traces, to which the two longer leads and the two short leads can be soldered to, in order to electrically connect each one of the short leads with a respective one of the long leads. Thus, prior approaches involve four leads having to be micro joined together to create a wound coil that can be electrically connected to a medical positioning system 14 or other device located at a proximal end of the catheter. A size of the leads extending from the wound coil and/or the longer leads to be micro joined together can be approximately 58 AWG, in some examples, which is 9.9 micrometers in diameter. Due in part to the small size of the leads, this step can require a specialized person and/or equipment to micro join the longer leads and the shorter leads together, which can result in excess time and resources being spent to manufacture a sensor coil assembly.

In contrast, embodiments of the present disclosure can reduce a time and/or resources required to manufacture the sensor coil assembly 38. For example, the first conductive wire segment 42, the second conductive wire segment 54, and the third conductive wire segment 56 can be formed from a unitary piece of wire and can include no joints between the first conductive wire segment 42 and the second conductive wire segment 54 and the first conductive wire segment 42 and the third conductive wire segment 56.

In some embodiments, the sensor coil assembly 38 can include one or more bobbins (also referred to as carrier members) configured for storing the second conductive wire segment 54 and/or the third conductive wire segment 56. For example, the sensor coil assembly 38 can include a first bobbin 59 and a second bobbin 60. In some embodiments, the second conductive wire segment 54 can be wrapped around the first bobbin 59 and the third conductive wire segment 56 can be wrapped around the second bobbin 60. Upon manufacture of the sensor coil assembly 38, the second conductive wire segment 54 and the third conductive wire segment 56 can have a length in a range from 5 centimeters to 500 centimeters. However, the length can be less than 5 centimeters or greater than 500 centimeters, in some embodiments. Due to a length and small diameter, the conductive wire segments 54, 56 can be problematic when storing, handling, and/or shipping the sensor coil assembly 38. For example, because of the small diameter, the conductive wire segments 54, 56 can be brittle and/or can easily break. A possibility for breakage of the conductive wire segments 54, 56 is compounded by the fact that conductive sire segments 54, 56 can be rather long in length. Accordingly, embodiments of the present disclosure can include the one or more bobbins configured for storing the second conductive wire segment 54 and the third conductive wire segment 56.

In some embodiments, the first bobbin 59 and/or the second bobbin 60 can include one or more winding channels. For example, the first bobbin 59 can include winding channel 66 and the second bobbin 60 can include winding channel 68. The first bobbin 59 and the second bobbin 60 can each have a central lumen. For example, the first bobbin 59 can have a central lumen 62 and the second bobbin 60 can have a central lumen 64. Further aspects of the first bobbin 59 and second bobbin 60 are illustrated in FIG. 2B, which is an isometric side view of the first bobbin 59 in FIG. 2A, which can be the same as second bobbin 60, in accordance with embodiments of the present disclosure.

FIG. 2B depicts an isometric end and side view of the first bobbin 59 resting on the second bobbin 60, which is displayed in an isometric end and top view.

The first bobbin 59 can have a longitudinal axis defined by line cc, which extends through the central lumen 62. In an example, the first bobbin 59 can include a hollow cylinder 74 formed around the longitudinal axis cc, which defines the central lumen 62. In some embodiments, a proximal radial lip 70 can extend from a proximal end of the hollow cylinder 74 and a distal radial lip 72 can extend from a distal end of the hollow cylinder 74. In some embodiments, the proximal lip 70 and the distal radial lip 72 can be parallel to one another. In some embodiments, the proximal lip 70 and the distal lip 72 can be divergent. In some embodiments, as the proximal lip 70 and the distal lip 72 extend from the hollow cylinder 74, the proximal lip 70 can be flared proximally and the distal lip 72 can be flared distally.

The proximal lip 70 and the distal lip 72 can define a winding channel 76 between the proximal lip 70 and the distal lip 72. The winding channel 76 and the hollow cylinder 74 can be coaxial with the longitudinal axis c-c of the first bobbin 59. In some embodiments, the winding channel 76 can have a constant width, as depicted in FIG. 2B, when the proximal lip 70 and the distal lip 72 parallel to one another. Alternatively, a width of the winding channel 76 can increase from a base of the winding channel 76 (e.g., next to the hollow cylinder 74) to an opening of the winding channel 76 (e.g., between an outer most perimeter of the proximal lip 70 and the distal lip 72), for example, when the proximal lip 70 and the distal lip 72 are flared. In some embodiments, a conductive wire segment (e.g., second conductive wire segment 54, third conductive wire segment 56) can be wound around an outer surface of the hollow cylinder 74 between the proximal lip 70 and the distal lip 72 in the winding channel 76.

In some embodiments, flaring of the proximal lip 70 and the distal lip 72 can allow for easier winding of the conductive wire segment onto the bobbin 59. For example, flaring of the proximal lip 70 and the distal lip 72 can help to guide the conductive wire segment into the winding channel 76, allowing for easier winding of the conductive wire segment onto the bobbin 59.

FIG. 2C is an isometric side view of an additional embodiment of the bobbins in FIG. 2A, in accordance with embodiments of the present disclosure. FIG. 2C depicts an isometric end and side view of a first multiple winding channel bobbin 80 resting on a second multiple winding channel bobbin 81, which is displayed in an isometric end and top view. As discussed in relation to FIGS. 2A and 2B, the first bobbin 59 and the second bobbin 60 can be separate bobbins. In some embodiments, the bobbins can be connected to one another and/or can be formed from a unitary piece of material, as depicted in FIG. 2C. In some embodiments, a multiple winding channel bobbin 80 can include more than one winding channel. For example, the multiple winding channel bobbin 80 can include a first winding channel 82 and a second winding channel 84. In some embodiments, the multiple winding channel bobbin 80 can include a hollow cylinder 86 disposed about and coaxial with a longitudinal axis defined by line d-d. In an example, the hollow cylinder 86 can include a central lumen that extends therethrough, as discussed in relation to the first bobbin 59.

In some embodiments, a proximal lip 87 can extend from a proximal end of the hollow cylinder 86, a distal lip 90 can extend from a distal end of the hollow cylinder 86, and a medial lip 88 can extend from the hollow cylinder 86 between the proximal end and the distal end of the hollow cylinder 86. In some embodiments, the winding channels 82, 84 can have constant widths. Alternatively, the winding channels 82, 84 can have increasing widths as they extend further radially from the longitudinal axis d-d. In an example, the proximal lip 87, the medial lip 88, and the distal lip 90 can be parallel to one another. Alternatively, in some embodiments, the lips can be divergent from one another. In some embodiments, the proximal lip 87 can be flared away from the medial lip 88, as it extends radially away from the longitudinal axis d-d. In some embodiments, the distal lip 90 can be flared away from the medial lip 88, as it extends radially away from the longitudinal axis d-d. Thus, the lips can define winding channels 82, 84 that have increasing widths as they extend radially away from the longitudinal axis d-d. As discussed herein, flaring of the proximal lip 87 and the distal lip 90 can help to guide the conductive wire segment into the winding channels 82, 84, allowing for easier winding of the conductive wire segment onto the multiple winding channel bobbin 80.

Figure 3:
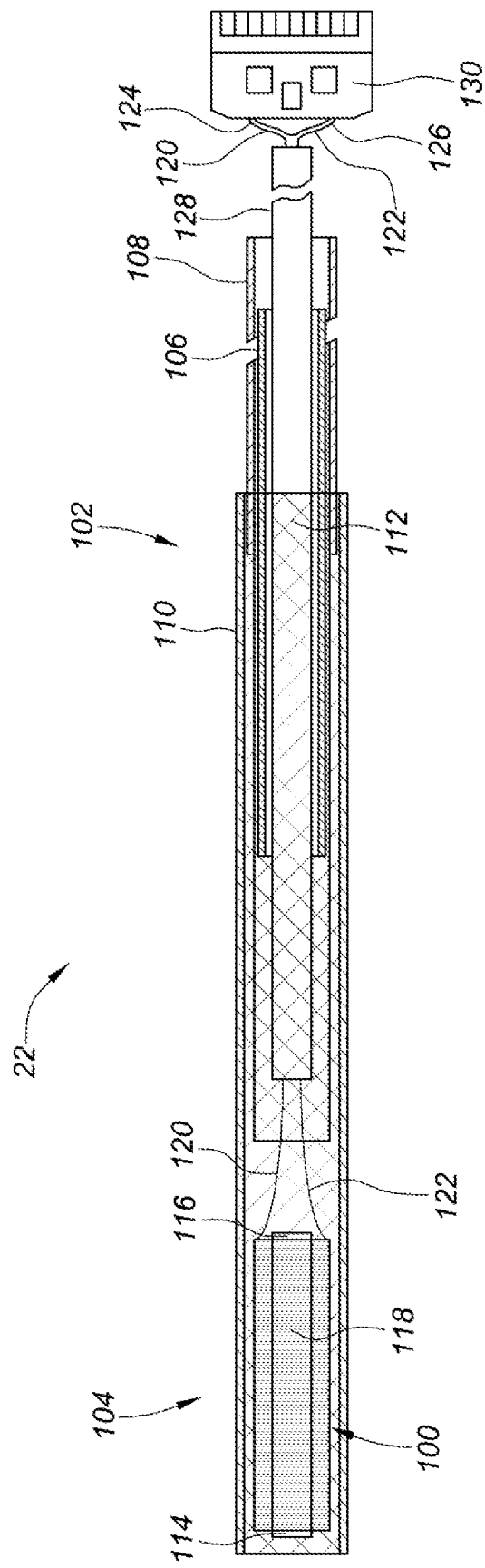
FIG. 3 depicts a cross-sectional side view of a catheter that includes a sensor coil, in accordance with embodiments of the present disclosure.

FIG. 3 is a cross-sectional side view of a catheter 12 that includes a sensor coil 100, in accordance with embodiments of the present disclosure. In some embodiments, the catheter 12 can include a shaft 22, which can be elongated and can include a proximal portion 102 and a distal portion 104. In some embodiments, the sensor coil 100 can be disposed in the distal portion 104 of the shaft 22. The shaft 22 can have a longitudinal axis that travels through a center of the shaft 22. In some embodiments, the sensor coil 100 can be disposed about the longitudinal axis, such that the shaft 22 is coaxial with the sensor coil 100. In some embodiments, the sensor coil 100 can be disposed at an angle to the longitudinal axis and/or can be disposed off-axis.

In some embodiments, the shaft 22 can be formed from one or more layers of material. For example, the shaft 22 can be formed from multiple layers of a polymer material. The shaft 22 can include a first inner polymer layer 106, a second polymer layer 108, and a third polymer layer 110. In some examples, the first polymer layer 106 can be an innermost layer, the second polymer layer 108 can be a middle polymer layer, and the third polymer layer 110 can be an outermost polymer layer. In some examples, the first polymer layer 106 can extend part way between the proximal portion 106 and the distal portion 104, the second polymer layer 108 can extend more distally than the first polymer layer 106, and the third polymer layer 110 can extend more distally than the second polymer layer 108. In some embodiments, the third polymer layer 110 can extend to the distal portion 104 and/or to a distal end of the shaft 22. In some embodiments, a braid layer 112 (e.g., wire braid layer) can be disposed around the second polymer layer 108 and the third polymer layer 110 can be disposed around the braid layer 112. The third polymer layer 110 can be an encapsulating layer that can encapsulate the braid layer 112, the second polymer layer 108, the first polymer layer 106, and any components included within a lumen formed by the first polymer layer 106. The encapsulating layer can provide a smooth surface for introduction of the shaft 22 into a vasculature of a patient. In some embodiments the encapsulating layer can be hydrophobic to further enable the shaft 22 to pass through the vasculature of a patient easily.

In some embodiments, as discussed herein, the sensor coil 100 can be disposed in the distal portion 104 of the shaft 22. The sensor coil 100 can be formed by wrapping a first conductive wire segment around a longitudinal axis. In some embodiments, the longitudinal axis can be shared with a longitudinal axis of the shaft 22. Alternatively, the longitudinal axis which the sensor coil is formed around can be disposed at an angle to the longitudinal axis of the shaft 22 and/or disposed off-axis. The sensor coil 100 can include a sensor core that includes a distal end 114 and a proximal end 116. The sensor coil 100 can be formed from a first conductive wire segment 118 wound around the sensor core. In an example, the first conductive wire segment 118 can be wrapped around the sensor core, as discussed herein. In some embodiments, multiple layers of windings can be formed by wrapping the sensor core with the first conductive wire segment 118 multiple times between the proximal end 116 and the distal end 114 of the sensor core. Alternatively, as discussed herein, the sensor coil 100 may not include a sensor core. For example, in some embodiments, a coreless sensor coil can be formed around a winding core, which can then be removed to form the coreless sensor coil.

In some embodiments, a second conductive wire segment 120 can extend from a first coil end of the first wire segment 118 and through the proximal portion 102. Additionally, a third conductive wire segment 122 can extend from the second coil end of the first wire segment 118 and through the proximal portion 102. In some embodiments, as discussed herein, the first conductive wire segment 118, the second conductive wire segment 120, and the third conductive wire segment 122 can be formed from a unitary piece of wire, as discussed herein. In some embodiments, the second conductive wire segment 120 can have a proximal end 124 and the third conductive wire segment 122 can have a proximal end 126. The proximal ends 124, 126 can be disposed at a proximal end of the shaft 22. In an example, no connections can be included along the first, second, and third conductive wire segment between the proximal end 124 of the second conductive wire segment 120 and the proximal end 126 of the third conductive wire segment 122. As discussed herein, this can prevent having to connect the first conductive wire segment 118 with the second conductive wire segment 120 and the third conductive wire segment 122.

In some embodiments, the first polymer layer 106 can form a lumen through which various componentry can be passed. In some embodiments, an elongated housing 128 can be passed through the lumen of the first polymer layer 106. The elongated housing 128 can extend from a proximal end of the shaft 22 and through the proximal portion 102. In some embodiments, the elongated housing 128 can extend into the distal portion 104 of the shaft 22. In an example, the elongated housing 128 can have a lumen through which the second conductive wire segment 120 and the third conductive wire segment 122 can be passed. In an example, the elongated housing 128 can be a flexible tube through which the second conductive wire segment 120 and the third conductive wire segment 122 can be passed. In some embodiments, the elongated housing 128 can include a shielding in walls of the elongated housing to shield the contents of the elongated housing 128 (e.g., second conductive wire segment 120 and the third conductive wire segment 122) from electromagnetic interference. For example, the elongated housing 128 can include a wire mesh layer in walls of the elongated housing 128.

In some embodiments, the second conductive wire segment 120 and the third conductive wire segment 122 can be twisted together to form a twisted pair. Forming a twisted pair with the second conductive wire segment 120 and the third conductive wire segment 122 can assist with cancelling out electromagnetic interference from external sources. In some embodiments, the second conductive wire segment 120 and the third conductive wire segment 122 can form a twisted pair within the elongated housing 128. For example, the second conductive wire segment 120 and the third conductive wire segment 122 can be untwisted outside of the elongated housing 128. The second conductive wire segment 120 and the third conductive wire segment 122 can have an insulative coating disposed around the conductive wire segments. The insulative coating can prevent an electrical short from occurring with respect to the conductive wire segments. In some embodiments, the twisted pair can have a wire gauge of approximately 50 AWG.

In some embodiments, the proximal end 124 of the second conductive wire segment 120 and the proximal end 126 of the third conductive wire segment 122 can extend from a proximal end of the catheter shaft 22 and a proximal end of the elongated housing 128. In some embodiments, a length between a proximal end of the elongated housing 128 and a distal end of the shaft 22 can be approximately 110 inches, although the length between the proximal end of the elongated housing 128 and the distal end of the shaft 22 can be less than or greater than 110 inches. In some embodiments, the proximal end 124 of the second conductive wire segment 120 can be stripped of wire insulation and the proximal end 126 of the third conductive wire segment 122 can be stripped of wire insulation. In some embodiments, a connector 130 can be connected to the proximal ends 124, 126 of the first and second conductive wire segments 120, 122. The connector 130 can connect the second conductive wire segment 120 and the third conductive wire segment 122 to a medical positioning system 14, in some embodiments. The elongated housing 128 can extend from the proximal end of the shaft 22 to, for example, the medical positioning system 14 and can protect the twisted pair.

Figure 4:
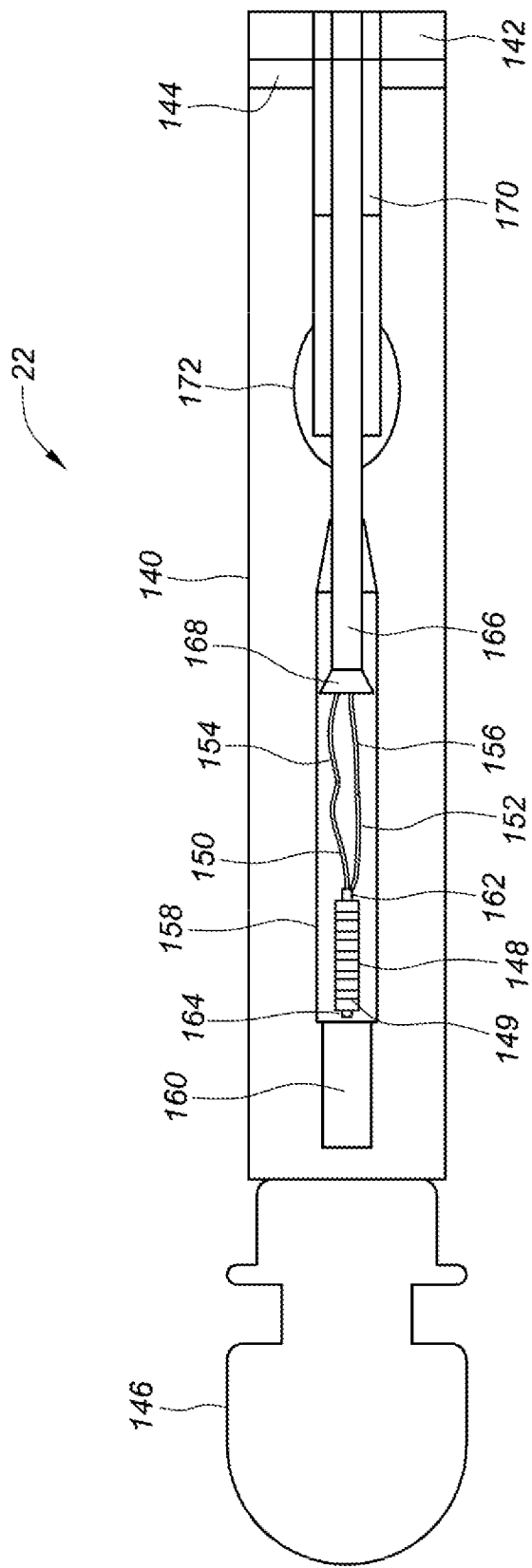
FIG. 4 depicts a cross-sectional side view of a catheter that includes a sensor coil, in accordance with embodiments of the present disclosure.

FIG. 4 is a cross-sectional side view of a catheter 12 that includes a sensor coil 110, in accordance with embodiments of the present disclosure. In some embodiments, the catheter 12 can include an elongated shaft 22 that includes a proximal portion 142 and a distal portion 140. The proximal portion 142 and the distal portion 140 can be connected to one another at an adhesive joint 144. In some embodiments, the elongated shaft 22 can include a distal tip 146. The distal tip 146 can, in some embodiments, be associated with a diagnostic and/or therapeutic device. For example, in some embodiments, the distal tip 146 can include one or more electrodes for sensing electrical signals associated with cardiac tissue, one or more ablation elements for performing therapy on cardiac tissue, an irrigation element, and/or other devices.

In some embodiments, the elongated shaft 22 can include a sensor coil 148 disposed in the distal portion 140 of the elongated shaft 22. The sensor coil 148 can be wound around a sensor core that includes a proximal end 162 and a distal end 164. As discussed herein, the sensor coil 148 can be coaxial with the elongated shaft 22, in some embodiments. The sensor coil 148 can be a wound coil formed from a first conductive wire segment 149. In some embodiments, the first conductive wire segment 149 can include a first coil end 150 and a second coil end 152. A second conductive wire segment 154 can extend from the first coil end 150 and a third conductive wire segment 156 can extend from the second coil end 152. In some embodiments, the second conductive wire segment 154 and the third conductive wire segment 156 can extend through the distal portion 140 and the proximal portion 142 of the elongated shaft 22 out a proximal end of the elongated shaft 22 and a proximal end 30 of the catheter 12. As discussed herein the first conductive wire segment 149, the first coil end 150, the second coil end 152, the second conductive wire segment 154, and the third conductive wire segment 156 can all be formed of a unitary piece of wire. In an example, the unitary piece of wire can include no connections between. For example, the unitary piece of wire is a single unbroken piece of wire that forms the first conductive wire segment 149, the first coil end 150, the second coil end 152, the second conductive wire segment 154, and the third conductive wire segment 156.

In some embodiments, the distal portion 140 and the proximal portion 142 of the shaft 22 can include a lumen in which various componentry can be inserted. For example, in some embodiments, the sensor coil 148, the second conductive wire segment 154, and the third conductive wire segment 156 can be inserted into the lumen. In some embodiments, the sensor coil 148 can be housed in a sensor coil housing 158. In an example, the sensor coil housing 158 can be formed of a flexible material. The sensor coil housing 158 can be formed of a polymer that is poured around the sensor coil assembly, the first coil end 150, second coil end 152, a portion of the second conductive wire segment 154, and/or a portion of the third conductive wire segment 156. In some embodiments, the sensor coil housing 158 can be inserted in a distal lumen of the distal portion 140 of the shaft 22.

In some embodiments, more than one sensing device can be included in the distal portion 140 of the shaft 22. For example, a second sensor 160 can be included in the distal portion 140 of the shaft 22. As depicted, the second sensor 160 can extend further distally than the sensor coil housing 158. In some embodiments, the second sensor can be a second sensor coil, an electrode, and/or a thermocouple.

In some embodiments, a braid layer 166 can extend from a proximal end of the sensor coil housing 158 through the distal portion 140 and through the proximal portion 142. In some embodiments, the braid layer 166 can extend from a proximal end 30 of the handle 20. In some embodiments a proximal end of the sensor coil housing 158 can be formed around a distal end of the braid layer 166 and can be tapered. Thus, the braid layer 166 can extend into the sensor coil housing 158. In some embodiments, the braid layer 166 can have a flared distal end 168. The flared distal end 168 can be formed to make it easier to insert the second conductive wire segment 154 and/or the third conductive wire segment 156 into the braid layer 166. In some embodiments, the flared distal end 168 can be formed to create an improved connection between the sensor coil housing 158 and the braid layer 166. For example, the sensor coil housing 158 can be formed around the distal end of the braid layer 166 and the flared distal end 168. As such, the flared distal end 168 can help secure the braid layer 166 to the sensor coil housing 158 to prevent the sensor coil housing 158 from being pulled apart from the braid layer 16.

In some embodiments, the second conductive wire segment 154 and the third conductive wire segment 156 can pass through the braid layer 166 and out a proximal end of the braid layer 166. In some embodiments, the braid layer 166 can shield the second conductive wire segment 154 and the third conductive wire segment 156 from electromagnetic interference, as discussed herein.

In some embodiments, an elongated housing 170 can extend from a proximal end of the shaft 22 and through the proximal portion 142. In some embodiments, the elongated housing 170 can extend into the distal portion 140 of the shaft 22. In an example, the elongated housing 170 can have a lumen through which the second conductive wire segment 154 and the third conductive wire segment 156 can be passed. In an example, the elongated housing 170 can be a flexible tube through which the second conductive wire segment 154 and the third conductive wire segment 156 can be passed. In some embodiments, the elongated housing 170 can include a shielding (e.g., braid layer 166) in walls of the elongated housing 170 to shield the contents of the elongated housing 170 (e.g., second conductive wire segment 154 and the third conductive wire segment 156) from electromagnetic interference. In some embodiments, the elongated housing 170 can extend from the distal portion 140, through the proximal portion 142, and from a proximal end 30 of the catheter 12.

In some embodiments, a glue joint 172 can be disposed at a distal end of the elongated housing 170. In an example, the glue joint 172 can secure the braid layer to the distal end of the elongated housing 170. In some embodiments, the glue joint 172 can encapsulate the distal end of the elongated housing 170, the braid layer 166, and the proximal end of the sensor coil housing 158. Alternatively, in some embodiments, the glue joint 172 can encapsulate the distal end of the elongated housing 170 and a portion of the braid layer 166 between the distal end of the elongated housing 170 and the proximal end of the sensor coil housing 158 can remain exposed, as depicted. In some embodiments of the present disclosure, the distal end of the elongated housing 170 can extend to the proximal end of the sensor coil housing 158. In some embodiments, the proximal end of the sensor coil housing 158 can be connected to the distal end of the elongated housing 170.

In some embodiments, pull wires can run longitudinally along the catheter shaft 22, from a handle 20, through the proximal portion 142, and into the distal portion 140. The pull wires can be selectively tensioned via an actuator in the handle 20. In some embodiments, one or more sensor coils can be disposed around the pull wires. In an example, the one or more sensor coils can be disposed around a longitudinal axis defined by each of the pull wires. For instance, when three pull wires are included in the catheter shaft 22, a sensor coil can be disposed around each one of the pull wires.

Figure 5:
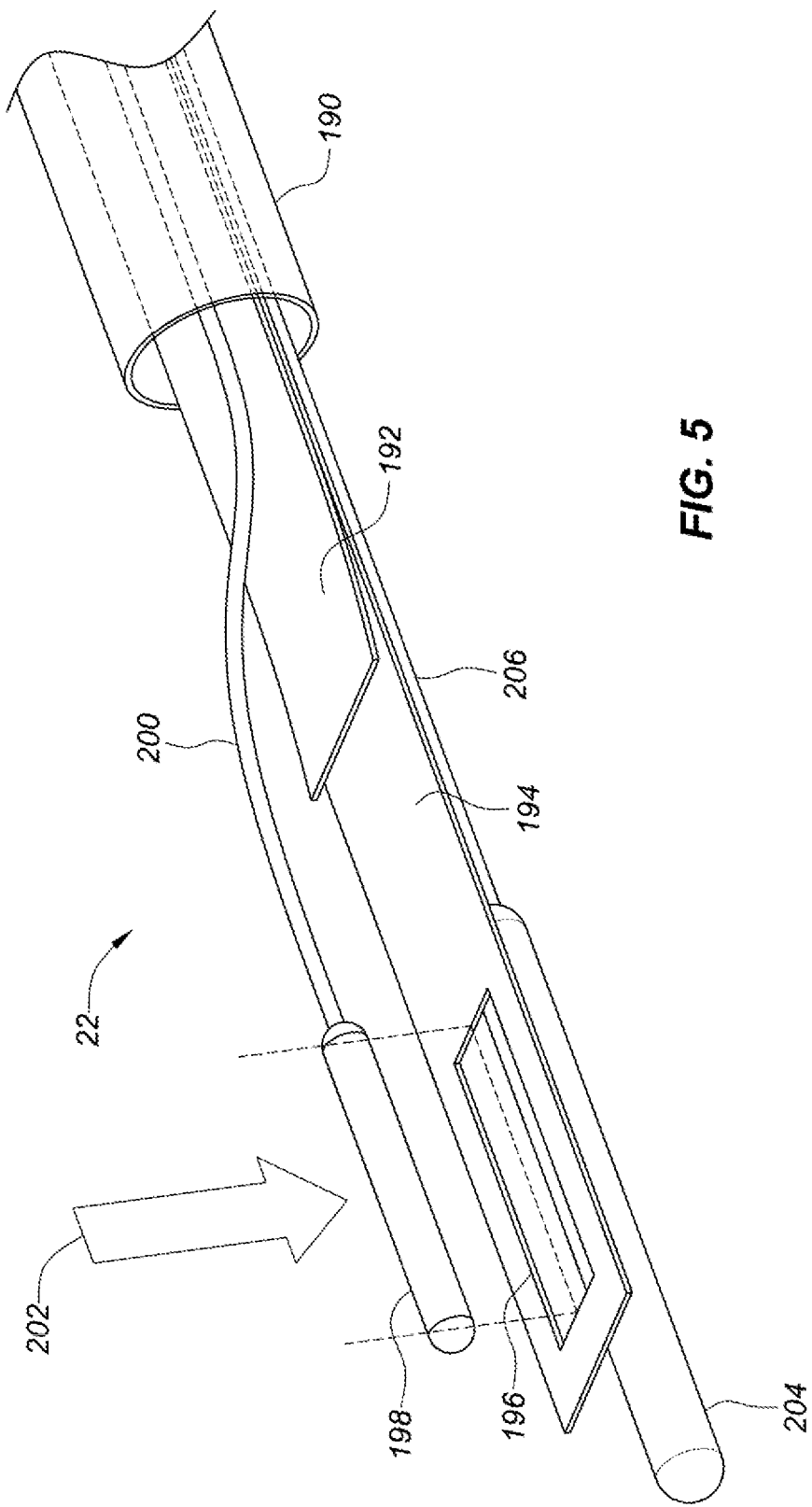
FIG. 5 depicts an isometric front, side, and top view of a sensor coil assembly being inserted into a distal portion of a catheter shaft, in accordance with embodiments of the present disclosure.

FIG. 5 is an isometric front, side, and top view of a sensor coil assembly being inserted into a distal portion 190 of a catheter shaft 22, in accordance with embodiments of the present disclosure. The distal portion 190 of the catheter shaft 22 can be connected to a proximal portion, which is connected to a handle 20. In an example, the catheter shaft 22 can include a first planarity member 192 and a second planarity member 194 that extends more distally than the first planarity member 192. The planarity members 192, 194 can provide for a unidirectional and/or a bidirectional functionality of the catheter shaft 22. A catheter shaft 22 can include a sensor coil housing 198, which can be connected to an elongated housing 200. The elongated housing 200 can extend through the distal portion 190 and the proximal portion of the catheter shaft 22. In an example, one of the planarity members (e.g., the second planarity member 194) can include a cutout 196. In some embodiments, the cutout 196 can be a longitudinal cutout sized and configured to fit the sensor coil housing 198. In an example, the cutout 196 can be a rectangular cutout that extends longitudinally along the second planarity member 194.

In some embodiments, the sensor coil housing 198 can be inserted into the cutout 196 in a direction of arrow 202. A distal end of the sensor coil housing 198 can abut with a distal end of the cutout 196 and a proximal end of the sensor coil housing 198 can abut with a proximal end of the cutout 196. In some embodiments, the sensor coil housing 198 can be inserted into the cutout 196 and an adhesive can be applied around an interface between the second planarity member 194 and the sensor coil housing 198. In some embodiments, upon insertion and/or securing of the sensor coil housing 198 in the cutout 196, the first planarity member 192, second planarity member 194, a second sensor coil housing 204 and sensor cable 206, the elongated housing 200, and the sensor coil housing 198 can be slid into the distal tube 190.

In some embodiments, the wound coil discussed in relation to FIG. 2A and the second conductive wire segment 54 and the third conductive wire segment 56 can be contained within the sensor coil housing 198 and the elongated housing 200. In some examples, the sensor coil assembly 38 can be stored and/or shipped using the bobbins 66, 68. The second conductive wire segment 54 and the third conductive wire segment 56 can be unwound from their respective bobbins 66, 68 and an assembly including the sensor coil housing 198 and the elongated housing 200 can be constructed.

Figure 6:
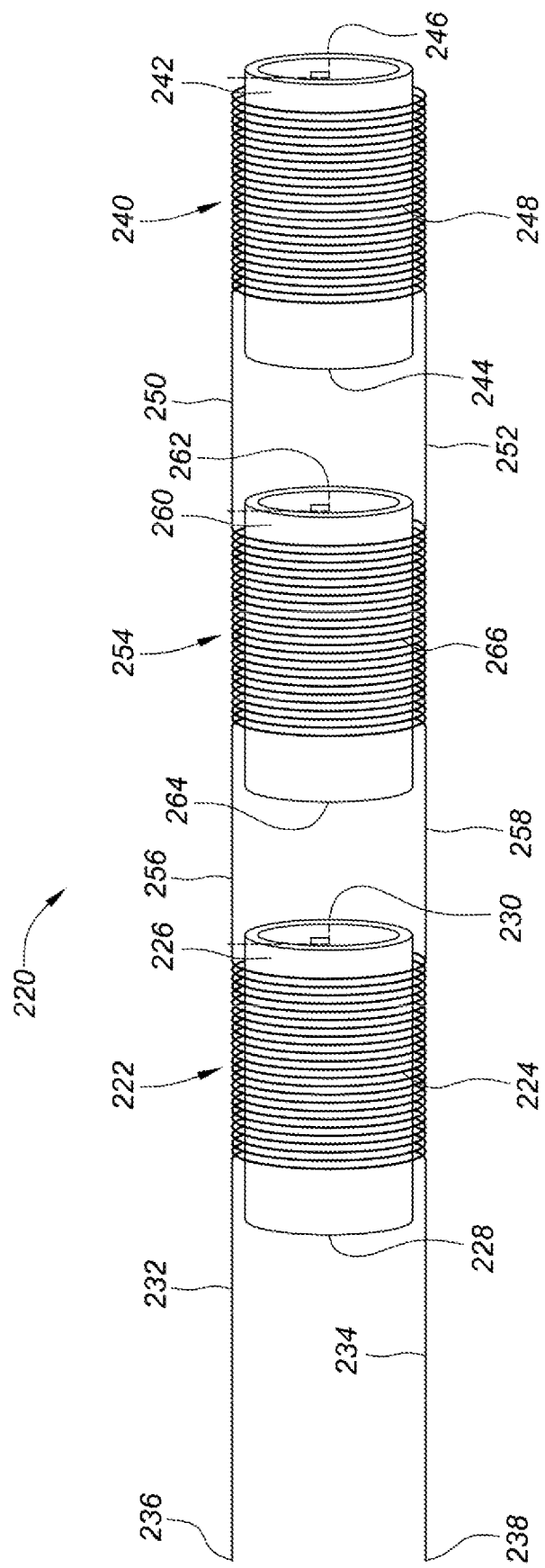
FIG. 6 depicts an isometric side and front view of a distributed sensor coil assembly, in accordance with embodiments of the present disclosure.

FIG. 6 is an isometric side and front view of a distributed sensor coil assembly 220, in accordance with embodiments of the present disclosure. In some embodiments, the distributed sensor coil assembly 220 can include an origin coil 222. The origin coil 222 can be formed from an origin conductive wire 224, in some embodiments. The origin conductive wire 224 can be wound around an origin sensor core 226 that includes a proximal end 228 and a distal end 230. In some embodiments, a first origin lead 232 and a second origin lead 234 can extend from a proximal end of the origin coil 222. The first origin lead 232 can have a proximal end 236 and the second origin lead 234 can have a proximal end 238. In some embodiments, as discussed in relation to FIGS. 2A and 2B, the first origin lead 232 and the second origin lead 234 can be wound around one or more bobbins, for storage, handling, and/or shipping.

In some embodiments of the present disclosure, the distributed sensor coil assembly 220 can include a terminal coil 240. The terminal coil 240 can be formed from the same origin conductive wire 224 that forms the first origin lead 232, the second origin lead 234, and the origin coil 222. The terminal coil 240 can include a terminal sensor core 242 that includes a proximal end 244 and a distal end 246. The terminal conductive wire 248 can be wound around the terminal sensor core 242 from the proximal end 244 to the distal end 246. In some embodiments, the terminal coil 240 can be formed with the terminal conductive wire 248, which is the same wire as the origin conductive wire 224 that forms the origin coil 222.

In some embodiments, the terminal coil 240 can include a first terminal lead 250 and a second terminal lead 252. The terminal leads 250, 252 can be electrically connected to the first origin lead 232 and the second origin lead 234. In a distributed sensor coil assembly that includes just the origin coil 222 and the terminal coil 240, a single wire can extend from a proximal end of the origin coil 222 (e.g., first origin lead 232) and can be wrapped around origin sensor core 226 (e.g., origin conductive wire 224) one or more times. The wire can then extend to the terminal coil 240 (e.g., first terminal lead 250) and can be wrapped around the terminal sensor core 242 one or more times (e.g., terminal conductive wire 248). The wire can then extend from the proximal end of the terminal coil 240 back to the origin coil 222 (e.g., second terminal lead 252). The wire can then be wrapped around the sensor core 226 one or more times (e.g., origin conductive wire 224) and can extend from the proximal end of the origin coil 222 (e.g., second origin lead 234). As such, one wire can be used to form a distributed sensor coil assembly.

In some embodiments, as the wire (e.g., second terminal lead 252) extends proximally from the terminal coil 240, the wire can extend from a distal end of the terminal coil 240 and may not be wrapped around the terminal sensor core 242, but may extend proximally straight back. In addition, in some embodiments, as the second terminal lead 252 extends proximally, it may not be wrapped around the origin sensor core 226, but may extend proximally straight back.

In some embodiments that include the origin coil 222 and the terminal coil 240, the pair of terminal leads 250, 252 can be connected to a distal end of the origin coil 222. In some embodiments, the pair of origin leads 232, 234 can have a first and second proximal end 236, 238, as discussed herein. The pair of origin leads 232, 234, the origin coil 222, the terminal leads 250, 252, and the terminal coil 240 can be formed from a unitary piece of wire. In some embodiments, there can be no connections between the first proximal end 236 and the second proximal end 238 of the origin leads 232, 234.

In some embodiments, as depicted, the distributed sensor coil assembly 220 can include a medial coil 254 disposed between the origin coil 222 and the terminal coil 240. In some embodiments, in relation to the medial coil 254, disposed between can mean that the medial coil 254 is spatially disposed between the origin coil 222 and the terminal coil 240 (e.g., as depicted in FIG. 6). In some embodiments, in relation to the medial coil 254, disposed between can mean that the medial coil 254 is electrically disposed between the origin coil 222 and the terminal coil 240 (e.g., as depicted in FIG. 6).

In some embodiments, the medial coil 254 can include a first medial lead 256 and a second medial lead 258 and a medial conductive wire 266. The medial conductive wire 266 can be wound around a sensor core 260 that has a proximal end 264 and a distal end 262. The pair of medial leads 256, 258 can be connected to a distal end of the origin coil 222. In some embodiments, the terminal leads 250, 252 can be connected to a distal end of the medial coil 254. As such, the origin leads 232, 234, the origin coil 222, the medial leads 256, 258, the medial coil 254, the terminal leads 250, 252, and the terminal coil 240 can be formed from a unitary piece of wire. For instance, no connections can be included between the proximal end 236 of the first origin lead 232 and the proximal end 238 of the second origin lead 234.

The origin coil 222, the medial coil 254, and the terminal coil 240 can be sized and configured for placement in a catheter. In some embodiments, by including multiple smaller coils (e.g., origin coil 222, medial coil 254, terminal coil 240), the coils can provide a same sensitivity as a longer coil in a magnetic field, while providing for a greater flexibility than a longer coil. For example, by including multiple smaller coils in a catheter shaft 22, as the catheter shaft 22 is deflected, the multiple smaller coils can move with respect to one another. In contrast, a longer coil that has a same cumulative length as the multiple smaller coils may not flex as readily as the multiple smaller coils. In some embodiments, the multiple smaller coils can be disposed around a central axis, as disclosed in U.S. publication no. 2014/0206985, which is hereby incorporated by reference. Prior methods for forming multiple smaller coils (e.g., 3 coils) can involve connecting multiple wire segments. In contrast no connections have to be made, according to embodiments of the present disclosure, when forming the distributed sensor coil assembly, because the multiple smaller coils are formed from a unitary piece of wire.

Figure 7:
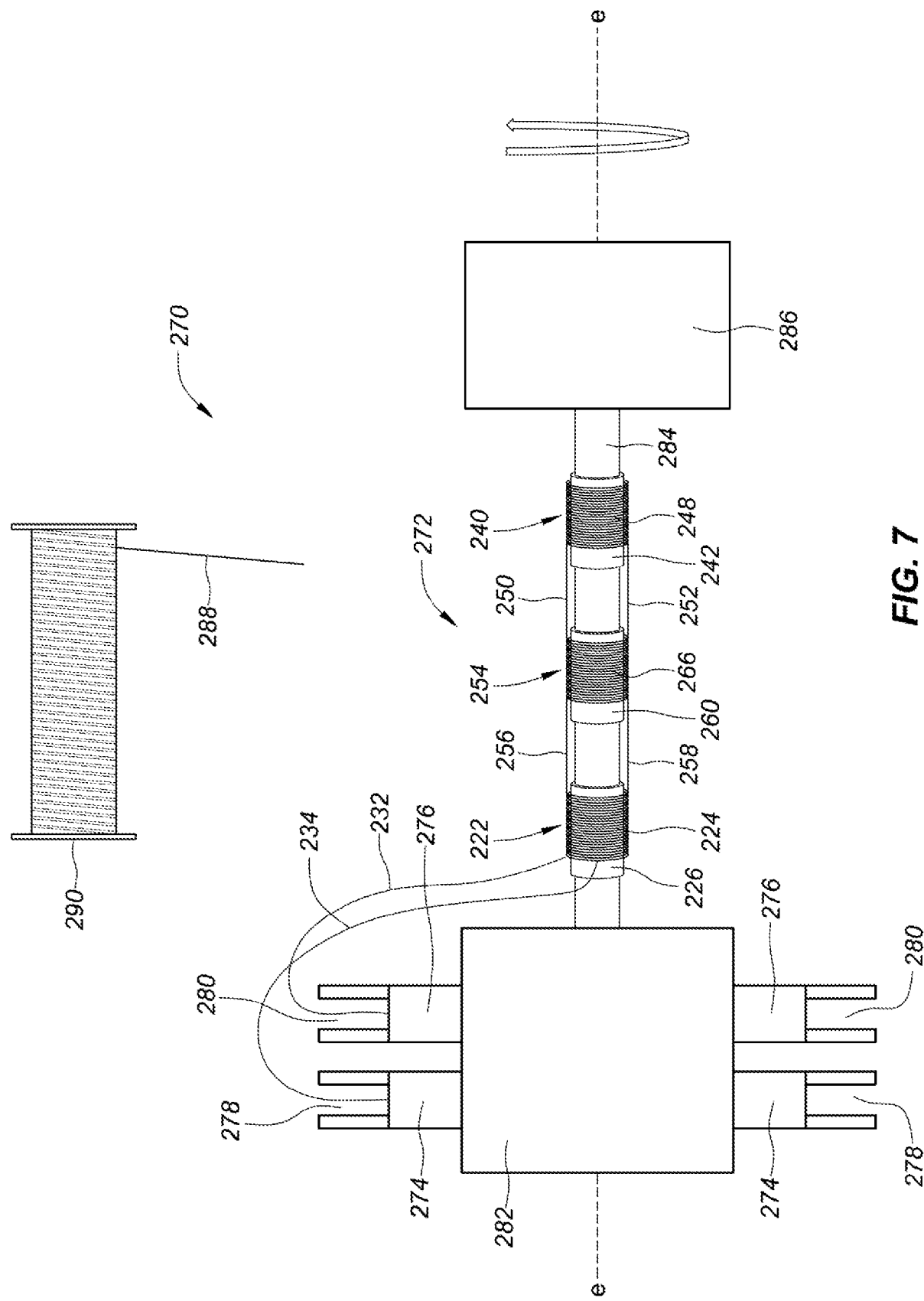
FIG. 7 depicts a cross-sectional view of a coil winding apparatus, in accordance with embodiments of the present disclosure.

FIG. 7 is a cross-sectional view of a coil winding apparatus 270, in accordance with embodiments of the present disclosure. In some embodiments, the coil winding apparatus 270 can be used to form a sensor coil assembly 272. In an example, the sensor coil assembly 272 can include an origin coil 222, medial coil 254, and a terminal coil 240. In some embodiments, the sensor coil assembly can include a first bobbin 274 and a second bobbin 276. In an example, a first origin lead 232 can be wrapped around the second bobbin 276 and a second origin lead 234 can be wrapped around the first bobbin 274. The origin leads 232, 234 can extend from a proximal end of the origin coil 222, which is formed from origin conductive wire 224. Medial leads 256, 258 can extend between the distal end of the origin conductive wire 224 and a proximal end of a medial conductive wire 266 that forms the medial coil 254. Terminal leads 250, 252 can extend between the distal end of the medial conductive wire 266 to a proximal end of a terminal conductive wire 248 that forms the terminal coil 240.

In some embodiments, the coil winding apparatus 270 can include a chuck 282, which can be a cylinder that can be rotated about a longitudinal axis, defined by line e-e in FIG. 7. In some embodiments, the coil winding apparatus 270 can be rotated by hand and/or can be connected to a powered drive (e.g., electric motor). In some embodiments, the first bobbin 274 and the second bobbin 276 can be connected to an outer radial surface of the chuck 282, as depicted in FIG. 7. In some embodiments, a spindle 284 can be connected to the chuck 282 such that it is coaxial with the longitudinal axis e-e and can be rotated with the chuck 282, the first bobbin 274, and the second bobbin 276. In some embodiments, an opposite end of the spindle 284 can be connected to a bearing member 286 to allow the spindle 284 to freely turn about the longitudinal axis e-e.

In some embodiments, the sensor coil assembly 272 can be constructed via the following procedure. In an example, sensor cores 226, 260, 242 can be placed on the spindle 284. In some embodiments, spacers can be placed on the spindle 284 between the sensor cores 226, 260, 242. The spacers can be hollow cylindrical segments, in some embodiments. Additionally, bobbins 274, 276 can be placed on the chuck 282. In some embodiments, it may be desired to construct a sensor coil that does not include a sensor core. As such, wire can be wound around a winding core and the winding core can be removed from the sensor coil to form a coreless sensor coil.

In some embodiments, the chuck 282 can be rotated, thus rotating the bobbins, 274, 276, the spindle 284, as well as components loaded onto the spindle (e.g., sensor cores, spacers, etc.). In some embodiments, as the chuck 282 is rotated, wire 288 from a spool 290 can be wrapped around one of the bobbins 274, 276 (e.g., second bobbin 276) to create a first origin lead 232 of a particular length. For example, the wire 288 can be wrapped around the second bobbin 276 in a winding channel 280 of the second bobbin 276. Upon loading the second bobbin 276 with the wire 288, the wire 288 can be wrapped around the origin sensor core 226 to form the origin coil 222. The wire 288 can be wrapped around the sensor core 226 one or more passes to create one or more layers of the origin conductive wire 224. The wire 288 can then be extended to the medial sensor core 260 to form a first medial lead 256 and the medial coil 254. Upon winding of the medial coil 254, the wire 288 can be extended to the terminal sensor core 242 to form the first terminal lead 250 and the terminal coil 240. The wire 288 can then be extended back to the medial sensor core 260 to form the second terminal lead 252 and, in some embodiments, form another layer of windings associated with the medial coil 254. The wire 288 can then be extended to the origin sensor core 226 to form the second medial lead 258 and, in some embodiments, form another layer of windings associated with the origin coil 222. The wire 288 can then be extended to the first bobbin 274 and wrapped around the first bobbin 274 in a winding channel 278 of the first bobbin 274 to form the second origin lead 234 of a particular length.

In some embodiments, after winding of the terminal coil 240, the wire 288 can be extended back to the first bobbin 274, instead of being wrapped around the medial sensor core 260 and/or the origin sensor core 226 and forming second terminal lead 252 and second medial lead 258. Thus, a direct lead can extend back to the first bobbin 274. In some embodiments, the second bobbin 276 (e.g., the bobbin positioned next to the sensor coil assembly 272) can be loaded with the wire 288 first. This can prevent pinching of the wire 288 when the first bobbin 274 is loaded with the wire 288 first and then the second bobbin 276 is loaded with wire 288. For example, if the first bobbin 274 is loaded with wire first, the wire 288 can be pinched in the winding channel 280 of the second bobbin 274, because the wire will have been passed over the winding channel 280 from the winding channel 278 of the first bobbin to form a sensor coil on the spindle 284.

In some embodiments, once winding of the sensor coil assembly 272 is completed, the spindle 284 can be removed from the chuck 282 and/or the bearing member 286 and the first bobbin 274, the second bobbin 276, as well as components loaded onto the spindle 284 (e.g., sensor cores, winding cores, spacers, etc.) can be removed from the spindle 284 (e.g., slid off of the spindle 284). The sensor coil assembly 272 can then be stored, shipped, and/or handled more easily through use of the first bobbin 274 and the second bobbin 276. In addition, because the sensor coil assembly 272 is constructed with a continuous wire, no connections between different portions of wire need to be soldered and/or connected in other ways, which can reduce an amount of resources needed to construct the sensor coil assembly 272.

In some embodiments, the coil winding apparatus 270 can be used to form a sensor coil assembly with a single sensor coil, as discussed herein. Alternatively, the coil winding apparatus 270 can be used for form a sensor coil assembly with more than three sensor coils. For example, one or more sensor cores and/or winding cores can be placed on the spindle 284 and wire 288 can be wound around the one or more sensor cores and/or winding cores to form a sensor coil assembly.

In some embodiments, when the first bobbin 274 and the second bobbin 276 are loaded with wire 288, and the sensor coil assembly has been wound, the sensor coil assembly can be removed from the coil winding apparatus 270. The first bobbin 274 and the second bobbin 276 can be connected to an additional apparatus, which can hold the sensor coils stationary, while rotating the first bobbin 274 and the second bobbin 276 to form a twisted pair from origin leads that extend from an origin coil to the first bobbin 274 and the second bobbin 276.

Figure 8:
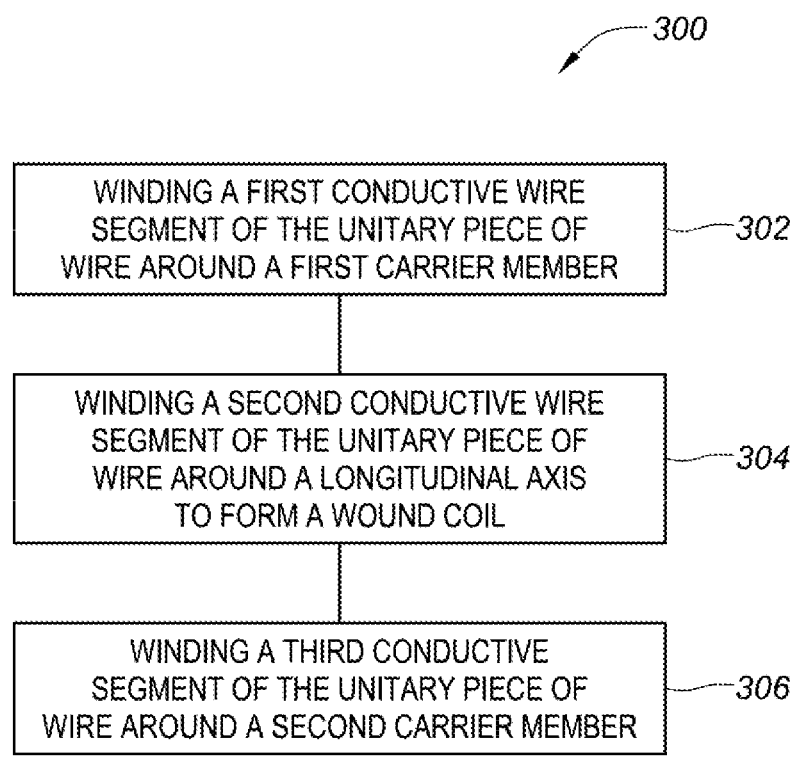
FIG. 8 depicts a flow diagram associated with a method for forming a sensor coil assembly from a unitary piece of wire, in accordance with embodiments of the present disclosure.

FIG. 8 depicts a flow diagram associated with a method for forming a sensor coil assembly from a unitary piece of wire, in accordance with embodiments of the present disclosure. In some embodiments, at block 302, the method can include winding a first conductive wire segment of a unitary piece of wire around a first carrier member (e.g., bobbin), as discussed in relation to FIG. 7. The carrier member can store the first conductive wire segment, thus protecting the first conductive wire segment from damage. This can be particularly beneficial when the piece of wire is of a 'small' size, such as that used for magnetic position sensors. For example, the unitary piece of wire can be approximately 58 AWG, as discussed herein. However, the size of the unitary piece of wire can be larger or smaller than 58 AWG.

At block 304, the method can include winding a second conductive wire segment of the unitary piece of wire around a longitudinal axis to form a wound coil. For example, the second conductive wire segment can be wound around an outer surface of a sensor core or may be wound around a longitudinal axis, but may not be wound around a sensor core, such that the wound coil is 'coreless'. The method can include winding a third conductive segment of the unitary piece of wire around a second carrier member, at block 306. For example, as discussed herein, the second carrier member can protect the third conductive segment of the unitary piece of wire from damage.

Embodiments are described herein of various apparatuses, systems, and/or methods. Numerous specific details are set forth to provide a thorough understanding of the overall structure, function, manufacture, and use of the embodiments as described in the specification and depicted in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment of a sensor coil assembly has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter, comprising:
   an elongated shaft, wherein the elongated shaft includes a proximal portion and a distal portion,
   a flexible planarity member disposed within the elongate shaft, wherein the flexible planarity member defines a longitudinal cutout;
   a positioning sensor comprising a unitary piece of wire that includes a first conductive wire segment, a second conductive wire segment, and a third conductive wire segment, wherein:
   the first conductive wire segment is wound around a longitudinal axis, forming a wound coil disposed in the distal portion of the elongated shaft, wherein the wound coil is disposed within the longitudinal cutout of the flexible planarity member and the flexible planarity member provides for unidirectional bending of the elongate shaft;
   the second conductive wire segment extends from a first coil end of the first wire segment and through the proximal portion of the elongated shaft; and
   the third conductive wire segment extends from the second coil end of the first wire segment and through the proximal portion.

2. The catheter of claim 1, wherein the second conductive wire segment and the third conductive wire segment are twisted together to form a twisted pair.

3. The catheter of claim 1, wherein the second conductive wire segment includes a proximal end and the third conductive wire includes a proximal end.

4. The catheter of claim 3, wherein no connections are included along the first, second, and third conductive wire segments between the proximal end of the second conductive wire segment and the proximal end of the third conductive wire segment.

5. The catheter of claim 3, wherein:
   the proximal end of the second conductive wire segment and the proximal end of the third conductive wire segment extend from a proximal end of the catheter shaft; and a connector is attached to the proximal end of the second conductive wire segment and the proximal end of the third conductive wire segment.

* * * * *